United States Patent
Feng et al.

(10) Patent No.: US 9,845,334 B1
(45) Date of Patent: Dec. 19, 2017

(54) HIGH-EFFICIENCY ORGANIC GLASS SCINTILLATORS

(71) Applicant: National Technology & Engineering Solutions of Sandia, LLC, Albuquerque, NM (US)

(72) Inventors: Patrick L. Feng, Livermore, CA (US); Joseph S. Carlson, Morgan Hill, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 0 days.

(21) Appl. No.: 15/289,611

(22) Filed: Oct. 10, 2016

Related U.S. Application Data

(60) Provisional application No. 62/356,996, filed on Jun. 30, 2016.

(51) Int. Cl.
*G01T 1/20* (2006.01)
*C07F 9/46* (2006.01)
(Continued)

(52) U.S. Cl.
CPC .............. *C07F 9/46* (2013.01); *C07C 209/08* (2013.01); *C07C 211/54* (2013.01);
(Continued)

(58) Field of Classification Search
CPC .............................. G01T 1/2018; G01T 1/208
See application file for complete search history.

(56) References Cited

U.S. PATENT DOCUMENTS

| | | |
|---|---|---|
| 7,064,228 B1 | 6/2006 | Yu et al. |
| 8,698,086 B2 | 4/2014 | Cherepy et al. |
| | (Continued) | |

FOREIGN PATENT DOCUMENTS

| | | |
|---|---|---|
| WO | 9940655 | 8/1999 |
| WO | 2012142365 A2 | 10/2012 |

OTHER PUBLICATIONS

Cai, et al., "Crtsyallization of Organic Glasses: Effects of Polymer Additives on Bulk and Surface Crystal Growth in Amorphous Nifedipine", In Pharmaceutical Research, vol. 28, Jun. 3, 2011, pp. 2458-2466.

(Continued)

*Primary Examiner* — Marcus Taningco
(74) *Attorney, Agent, or Firm* — Medley, Behrens & Lewis, LLC

(57) ABSTRACT

A new family of neutron/gamma discriminating scintillators is disclosed that comprises stable organic glasses that may be melt-cast into transparent monoliths. These materials have been shown to provide light yields greater than solution-grown trans-stilbene crystals and efficient PSD capabilities when combined with 0.01 to 0.05% by weight of the total composition of a wavelength-shifting fluorophore. Photoluminescence measurements reveal fluorescence quantum yields that are 2 to 5 times greater than conventional plastic or liquid scintillator matrices, which accounts for the superior light yield of these glasses. The unique combination of high scintillation light-yields, efficient neutron/gamma PSD, and straightforward scale-up via melt-casting distinguishes the developed organic glasses from existing scintillators.

20 Claims, 8 Drawing Sheets

(51) Int. Cl.
C09K 11/06 (2006.01)
C07F 7/08 (2006.01)
C07C 209/08 (2006.01)
C07C 211/54 (2006.01)
G01T 3/06 (2006.01)

(52) U.S. Cl.
CPC .......... *C07F 7/0809* (2013.01); *C07F 7/0827* (2013.01); *C09K 11/06* (2013.01); *G01T 1/20* (2013.01); *G01T 3/06* (2013.01); *C09K 2211/1011* (2013.01); *C09K 2211/1014* (2013.01)

(56) References Cited

U.S. PATENT DOCUMENTS

| | | | |
|---|---|---|---|
| 2013/0299702 A1 | 11/2013 | Zaitseva et al. | |
| 2014/0166889 A1* | 6/2014 | Kang | C03C 4/12 250/366 |
| 2015/0323683 A1* | 11/2015 | Vasilyev | G01V 5/107 250/269.1 |
| 2016/0104843 A1* | 4/2016 | Kobayashi | H01L 51/006 136/254 |

OTHER PUBLICATIONS

Cha, et al., "New Spiro[benzotetraphene-fluorene] Derivatives: Synthesis and Application in Sky-Blue Fluorescent Host Materials", In Journal of Fluorescence, vol. 24, May 25, 2014, pp. 1215-1224.

Kim, et al., "Blue OLEDs Utilizing Spiro[fluorene-7,9'-benzofluorene]-type Compounds as Hosts and Dopants", In Bull. Korean Chem. Soc., vol. 30, No. 3, Jan. 28, 2009, pp. 647-652.

Powell, et al., "Fracture of Molecular Glasses Under Tension and Increasing Their Fracture Resistance With Polymer Additivies", In Journal of Non-Crystalline Solids, vol. 429, 2015, pp. 122-128.

Salbeck, et al., "Spiro Linked Compounds for Use as Active Materials in Organic Light Emitting Diodes", In Macromolecular Symposia, vol. 125, 1997, pp. 121-132.

Wu, et al., "Synthesis of Amorphous Monomeric Glass Mixtures for Organic Electronic Applications", In Journal of Organic Chemistry, vol. 80, 2015, pp. 12740-12745.

Wei, et al., "Properties of Fluorenyl Silanes in Organic Light Emitting Diodes", In Chemistry of Materials, vol. 22, 2010, pp. 1724-1731.

\* cited by examiner

HIGH-EFFICIENCY ORGANIC GLASS SCINTILLATORS

CROSS-REFERENCE TO RELATED APPLICATIONS

This application claims priority to U.S. Provisional 62/356,996, filed on Jun. 30, 2016, which is hereby incorporated by reference in its entirety.

GOVERNMENT RIGHTS

This invention was made with Government support under Contract No. DE-AC04-94AL85000 between Sandia Corporation and the U.S. Department of Energy. The Government has certain rights in the invention.

BACKGROUND

An ongoing objective in the field of organic radiation detection materials is to achieve a balance between scintillation performance characteristics and cost. Organic molecular crystals possess superior light-yields and neutron/gamma pulse-shape discrimination (PSD), but are expensive to produce in large sizes. In contrast, liquid and plastic scintillators are readily scalable to large sizes, although both are characterized by reduced light yields and particle discrimination properties. For example, the brightest (non-PSD) plastic scintillators possess light yields of about 10,400 photons/MeVee, which is approximately 80% that of solution-grown trans-stilbene crystals. The light yields of PSD-capable plastics are about 8600 photons/MeVee, which is roughly 65% that of trans-stilbene crystals. Thus, there is a need for improved low-cost, large scintillators.

SUMMARY

The materials disclosed herein are engineered to provide luminescent organic glasses for the detection of gamma and fast neutron radiation. These materials can resist crystallization upon cooling, which results in the formation of stable, transparent glasses. This has beneficial implications for the preparation of low-cost/large-scale scintillators. Another breakthrough represented by the materials disclosed herein is the observation of high scintillation light yields of at least 1.5-3 times that of trans-stilbene, which is one of the brightest known organic scintillators (but is high-cost). The field of organic electronics may also benefit from these materials due to similar requirements, including high luminosity, high electron/hole mobility, and stable film-forming properties.

In an embodiment, a glass scintillator material comprises: a compound that includes a central species selected from the group consisting of: silicon, phosphorus, nitrogen, tin, germanium; an oxide, salt, or alkyl salt of silicon, phosphorus, nitrogen, tin, or germanium; or a rotationally symmetric organic species, or combination of any of these. A luminescent organic group is bonded to the central species or to an optional organic linker group. The optional organic linker group, if present, is bonded to the central species and the luminescent organic group, and the compound is in the form of an amorphous glass and is capable of generating luminescence in the presence of ionizing radiation.

In an embodiment, a method of making a compound, comprises: functionalizing a luminescent organic group; reacting the functionalized luminescent organic group with a central species to produce a compound with tripodal or tetrahedral geometry wherein one or more of the luminescent organic groups are bonded to the central species. The central species is selected from the group consisting of: silicon, phosphorus, nitrogen, tin, germanium; an oxide, salt, or alkyl salt of silicon, phosphorus, nitrogen, tin, or germanium; or a rotationally symmetric organic species, or combination of any of the these. The luminescent organic group is selected to inhibit pi-pi stacking of the compound.

In an embodiment of a method for conducting scintillation, the method comprises generating luminescence with a glass scintillating compound in the presence of ionizing radiation. The glass scintillating compound includes a central species selected from the group consisting of: silicon, phosphorus, nitrogen, tin, germanium; an oxide, salt, or alkyl salt of silicon, phosphorus, nitrogen, tin, or germanium; or a rotationally symmetric organic species, or combination of any of these. A luminescent organic group is bonded to the central species or to an optional organic linker group. The optional organic linker group if present is bonded to the central species and the luminescent organic group. The compound is in the form of an amorphous glass and is capable of scintillation. The method also includes detecting photons from the glass scintillating compound with a photodetector.

DETAILED DESCRIPTION

High-symmetry organic crystals that are based upon molecules that possess local $C_3$-symmetry have been reported. Increased molecular and crystallographic symmetry leads to significantly higher light yields and PSD relative to their respective low-symmetry parent fluorophore. High-symmetry space groups are also associated with improved crystal growth properties and mechanical robustness due to the presence of a greater number of independent slip systems to dissipate stresses induced by thermal or mechanical stimuli. The glass materials disclosed herein are constructed based on design criteria for analyzing and developing materials with compounds based upon luminescent groups arranged around a central atom or central moiety that display surprising scintillating properties, particularly for a glass-like material. In one embodiment, luminescent groups are bonded in a configuration as to disrupt pi-pi stacking, and thereby raising the kinetic barrier for crystallization to occur. In another embodiment, or in combination with the embodiment above, steric bulk can be introduced on or near the luminescent groups to disrupt pi-pi stacking. In another embodiment or in a combination with the embodiment above, the benzylic carbons of the ligands are modified to result in improved properties.

Figure 1:
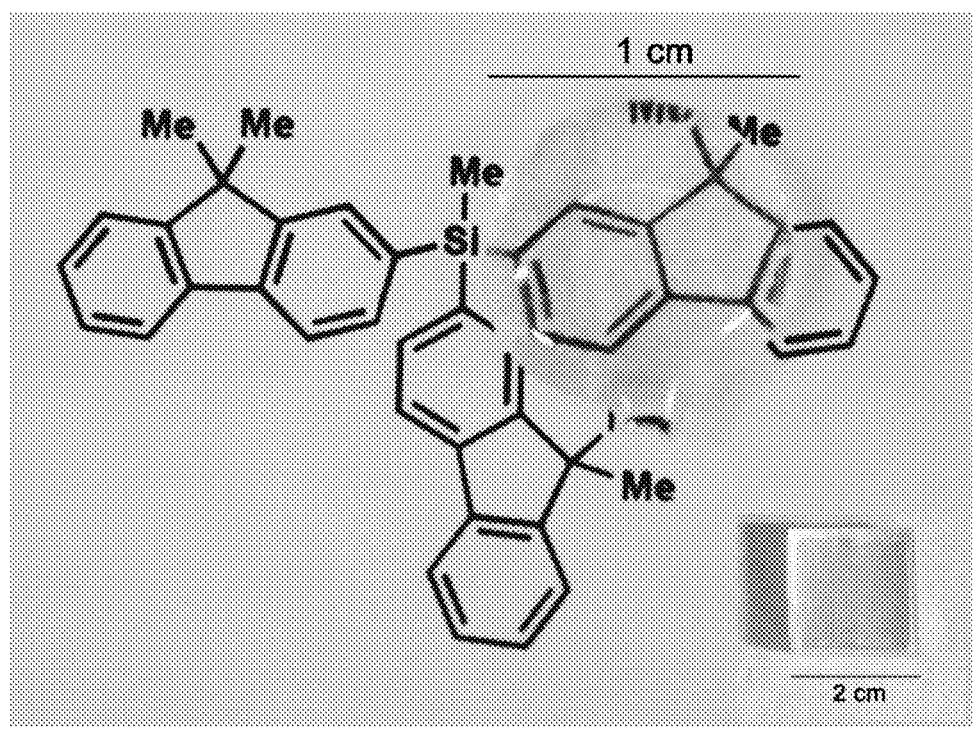
FIG. 1 is a photograph of two forms of Example 1B. The 1 cm, top circular material was drop-cast from the liquid, whereas the 2 cm cube shown in the inset was melted and cooled in a silicone mold.

Initial photophysical characterization of these materials showed that they behave as efficient scintillators in their respective crystalline forms; however, an unexpected finding was that they also form stable and highly transparent organic glasses following cooling of the melt (See photos in FIG. 1). Photoluminescence, thermoanalytical analysis, and scintillation measurements were performed to assess these materials and benchmark their performance against well-known organic scintillators. The combined results indicate that stable organic glasses present a promising new route towards high light-yield and low-cost PSD scintillators.

The materials described herein provide a new class of organic-based scintillators that combines several of the desirable attributes of existing crystalline, liquid, and plastic organic scintillators. The prepared materials may be isolated in single crystalline form or melt-cast to produce highly transparent glasses that have been shown to provide high light yields of 12,000 to 40,000 photons/MeVee, 13,000 to 20,000, or 16,000 to 18,000 photons/MeVee as determined with a trans-stilbene reference. In embodiments, the materials described herein exceeds the light yield of EJ-200 plastic scintillators and solution-grown trans-stilbene crystals. The prepared organic glasses exhibit neutron/gamma pulse-shape discrimination (PSD) and are compatible with wavelength shifters to reduce optical self-absorption effects that are intrinsic to pure materials such as crystalline organics. In an embodiment, the amorphous glass is capable of both neutron and gamma pulse-shape discrimination at 33 keVee to 30 MeVee, such as 100 to 1000 keVee, or 250 to 500 keVee. Overall, the glass scintillators are capable of generating luminescence in the presence of ionizing radiation, such as radiation at energy levels of 1,000 eVs to 30,000 eVs. The combination of high scintillation efficiency, PSD capabilities, and facile scale-up via melt-casting distinguishes this new class of amorphous materials from existing alternatives.

The glass scintillator material disclosed herein includes a central atom or species and one or more luminescent organic groups bonded to atom or species. The disclosure herein focuses primarily on the development and properties of optically transparent organic glass scintillators that are based upon a silicon central atom surrounded by three functionalized fluorene chromophores. However, the organic glass scintillators disclosed herein are not limited to this specific case and can be extended to other classes of compounds.

In an embodiment, the central atom or species of the compound may be silicon, phosphorus, nitrogen (as the free base or salt), tin, or germanium. These atoms were determined to be conducive to a tetrahedral or tripodal geometry and to the other desired criteria of the overall materials, i.e., glass-like and possessing scintillating properties.

In an embodiment, the central atom or species (nitrogen, silicon, phosphorous, tin or germanium) can be at any one of its stable oxidation states. The central atom or species may also be an oxide of any of these or in a salt or alkyl salt form.

An example of an oxide would include phosphorous as the tri-substituted phosphine or phosphine oxide.

In an embodiment, the central moiety can include multiple bonded atoms. For example, rotationally symmetric organic species can be selected for the central species of the compound. These include, for example, aliphatic, aromatic, heteroaromatic or polycyclic aromatic central groups, such as adamantane, tri-substituted benzene, truxene, triphenylene, spiro-bifluorene, and analogs thereof. Analogs thereof may, for example, include substitutions of hydrogen atoms or units of unsaturation with alkyl, aryl, heterocycles, halogens, or heteroatoms of type $BR_2$, $B(OR)_2$, $NR_2$, OR where R is alkyl or aryl. The alkyl groups, may, for example, be straight, branched or cyclic, and have 1 to 20 carbon atoms. The aryl groups may, for example, have five to twenty carbon atoms in the ring structure.

The compounds disclosed herein comprise luminescent organic groups that are bonded to the central atom or species. Organic generally means the elements of life, and encompasses carbon containing compounds and may also include oxygen, nitrogen, sulfur, phosphorous, halogens, and alkali metals. In an embodiment, the luminescent organic group comprises an aromatic species that is a chromophore. In an embodiment, the luminescent group is a polycyclic or polycyclic aromatic group.

In an embodiment, the luminescent organic group comprises, for example, fluorophores selected from terphenyl, trans-stilbene, naphthalene, anthracene, truxene, triphenylene, 1,3,5-triphenylbenzene, spirobifluorene, fluorene, carbazole, coumarin, anthracene, naphthalene, biphenyl, coumarin, phenyloxazole, phenyloxadiazole and analogs thereof. Analogs thereof may, for example, include substitutions of hydrogen atoms or units of unsaturation with alkyl, aryl, heterocycles, halogens, or heteroatoms of type $BR_2$, $B(OR)_2$, $NR_2$, OR where R is alkyl or aryl.

In certain embodiments, the luminescent organic groups are selected from functionalized organic chromophores that intrinsically behave as a scintillator. These compounds may include, for example, compounds such as:

(C3-symmetric examples): truxene, triphenylene, 1,3,5-triphenylbenzene, and analogs thereof.

(Non-C3-symmetric examples): Spirobifluorene, fluorene, carbazole, coumarin, anthracene, naphthalene, biphenyl, coumarin, phenyloxazole, phenyloxadiazole and analogs thereof.

The term "analogs thereof" is defined as above. The aryl groups may, for example, have five to twenty carbon atoms in the ring structure.

These examples typically are chemically modified (e.g., derivatized) to prevent spontaneous recrystallization upon cooling. Effective strategies to this end include the incorporation of linear or branched alkyl groups, or heteroatoms of type $BR_2$, $B(OR)_2$, $NR_2$, OR where R is alkyl or aryl. In an embodiment, the alkyl groups, aryl groups, or R groups may, for example, have 1 to 20, 5 to 18, or 6 to 16 carbon atoms.

Additional examples of fluorophore groups that may be attached to symmetric organic central moieties may comprise a wide range of known scintillating molecules, including, but not limited to: the structures (I) to (IX) below, 2,5-diphenyloxazole, 9,9'-dialkylfluorene, 9,9'-diarylfluorene, aryl- and/or alkyl substituted diarylfluorene such as is shown in structure I below (in particular, 2-aryl-9,9'-dialkylfluorene, 2-aryl-9,9'-diarylfluorene,) 7-aryl-9,9'-dialkylfluorene, 7-aryl-9,9'-diarylfluorene, 7-alkyl-9,9'-dialkylfluorene, 7-alkyl-9,9'-diarylfluorene, 9,10-diphenylanthracene, 2,5-diphenyl-1,3,4-oxadiazole, p-terphenyl, salicylic acid, and methyl salicylate, and analogs thereof (as defined above).

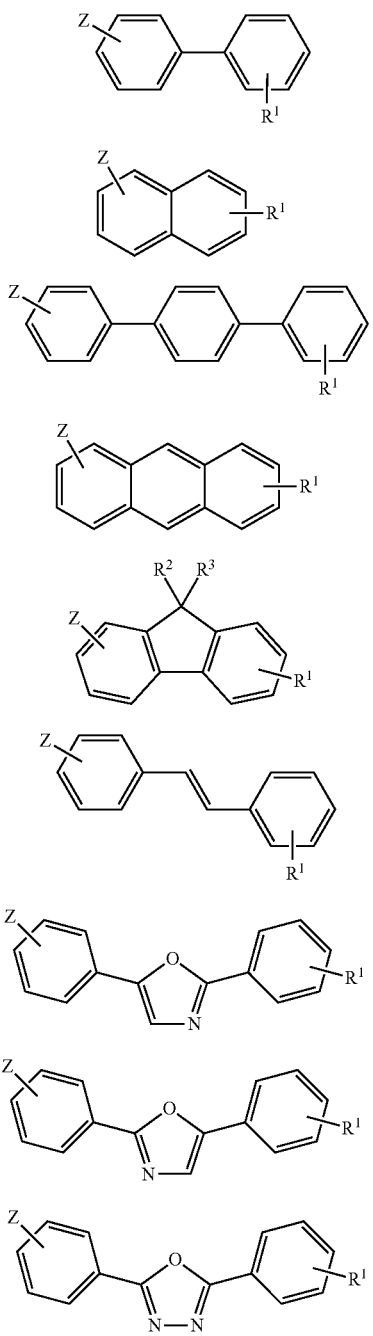

In structure (I) to (IX) Z is the central atom or species. $R^1$ is H, alkyl, alkoxy, aryl, aryloxy, B(aryl)$_2$, B(alkoxy)$_2$, N(alkyl)$_2$, or a halogen. The alkyl, alkoxy, aryl, and aryloxy groups may contain 1 to 20, 5 to 18, or 6 to 16 carbon atoms. $R^2$ and $R^3$ may be independently selected from alkyl groups, F, and oxygen. The hovering bond of Z and $R^1$ denotes that substitution can be at any point on the ring.

In an embodiment, the luminescent organic group may comprise, for example, functionalized fluorene or oxadiazole fluorophores. In particular, these groups may be paired with amine, silicon or phosphine oxide central species.

In an embodiment, each luminescent organic group may have a number average molecular weight of 100 to 2,500 Dalton (g/mol), such as 300 to 1200 Dalton, or 500 to 1000 Dalton.

In an embodiment, the luminescent organic group comprises a polycyclic group comprising one or more benzylic carbons and at least one benzylic carbon is substituted with an organic group. In an embodiment, the benzylic carbon that is substituted is a double benzylic carbon. The organic group may be an alkyl group, for example, a linear 1 to 6, branched, cyclic, or aromatic group, having 1 to 20 carbon atoms, such as 4 to 15, or 5 to 8 carbon atoms. As explained further below the organic group on the one or more benzylic carbons should be selected to inhibit pi-pi stacking in the compound.

In an embodiment, there is a linker atom or group between the central atom/moiety and the fluorophore. The linker group can be a linear or branched alkyl, aryl, heteroaryl, heteroalkyl group, or combinations thereof. The linker group is an optional component of the compound. Representative examples are depicted in structure (X) to (XII).

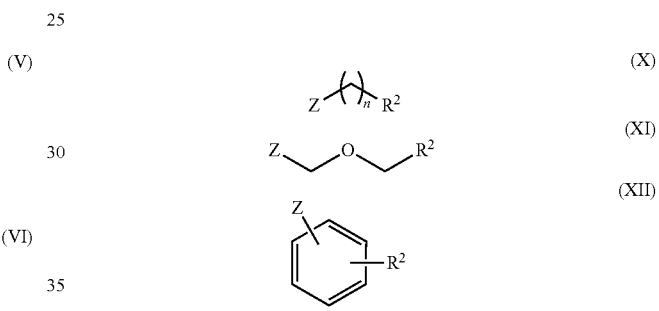

wherein Z is the central species or atom, n=1-5, and R is the fluorescent organic group.

Two general methods have been used to obtain molecules that form glassy states: (1) design of an overall three-dimensional structure that prevents efficient pi-pi stacking interaction, which can include luminescent organic groups arranged in a tetrahedral or spirocyclic configuration; and (2) the presence of bulky functional groups either directly attached, or two to three bonds away from the luminescent organic group that prevents efficient pi-pi stacking interaction. This selection criteria can produce compounds amenable to forming a stable glassy state despite the native fluorophore not able to form a stable glassy state.

More particularly, techniques or predictors disclosed herein found to affect the compound's ability for high scintillation and to resist crystallization are (a) selecting luminescent groups that have high quantum yields, and (b) selecting a central atom or species with a particular bond length and angle with the luminescent groups (e.g., tetrahedral or tripodal geometries), and (c) choosing appropriate functionality on the non-aromatic portion of the molecule to inhibit aromatic stacking.

The central atom and luminescent organic groups should be selected to result in stable organic glasses following cooling of the melt. The luminescent organic group can be added through symmetry modification of the compound (i.e. C3 rotational symmetry element) or the chemical functionalization of the compound to confer resistance to crystallization upon cooling (i.e. addition of aliphatic, alkoxy-, or other functional groups).

The selection of the luminescent organic group also has implications for the electronic properties of the glass, particularly with respect to the electron and hole mobilities. These properties are important for neutron/gamma pulse-shape discrimination (PSD), which is a widely used technique for the detection of special nuclear materials.

In an embodiment, the central atom or moiety and the luminescent organic groups are selected to produce a compound with as high a glass transition temperature (Tg) as possible. Embodiments with higher Tgs produce less transient effects and are typically more stable. In another embodiment, the central atom or moiety and the luminescent organic groups may have a low Tg. At or above the Tg, crystallization may occur, but the radioluminescent properties may improve as well. Compact luminescent groups typically predict a higher Tg and form a molecular structure with a roughly spherical shape.

In an embodiment, the glass-like scintillating compound has a trigonal pyramidal or tetrahedral structure that is tripodal with the luminescent organic group substitutions, i.e., three substitutions with luminescent organic groups and optionally has a fourth organic substituted group (not necessarily a luminescent group). In a particular embodiment, the fourth organic group is an oxygen atom and is bonded to a phosphorous central atom.

Representative trigonal pyramidal or tetrahedral structures for the glass scintillator are shown in the Additional Example Compound Structures sub-section of the Examples Section below. Many examples of which exhibit high resistance towards crystallization.

An additional distinction of the molecules shown in the example structures disclosed herein is that they typically exhibit high melting temperatures of greater than 150° C. and relatively high glass transition temperatures (Tg) of 50° C. to 160° C. This is in contrast with many amorphous organic materials, such as polymers (high molecular weight compounds) and organogels, which make use of long alkyl chains to attain a stable amorphous phase. Compared to the compact luminescent glasses described herein, polymers and organogels contain large regions of non-fluorescent moieties, which limit their application for use as an organic scintillator.

It is also possible to modify the glass-forming properties of the glass scintillator compound by controlled substitution of the different positions of the molecule. Using the silyl-based compounds as an example, it was discovered that a less bulky group, such as, for example, a linear hydrocarbon, at the axial silicon site leads to glasses that are more resistant towards crystallization, whereas bulky hydrocarbons tend to possess higher Tg values but also the potential to recrystallize over time. Modification of the benzylic carbon in the case of the fluorene-based fluorophores, leads to profound changes in thermal properties. A change from gem-dimethylfluorene to gem-dipropylfluorene (gem as known to those of skill in the art means "geminal," and indicates a relationship of two groups attached to the same carbon) groups results in a decrease in Tg from 93° C. to 55° C. Separately, insertion of a benzene group between the silicon atom and the 2-fluorene position of the ligands has been shown to increase the Tg to 130° C., while retaining the intrinsic amorphous properties of the material.

The geometry of the scintillator can also be manipulated to resist aromatic stacking by partial substitution of the central atom, for example, compounds that are based on a central atom or species that has only been di-substituted with the fluorescent groups. While this has been shown to result in generally lower glass transition temperatures than the tri- and tetra-substituted analogs, this method is an alternate route to prepare the glass scintillator materials.

In an embodiment, the luminescent organic groups need not be identical to each other, i.e. the compound may be configured to have different luminescent organic groups, which may or may not undergo intramolecular energy transfer between them. The potential advantages of this approach are to increase the scintillation light yield, further modify the melt and glass-formation properties, and/or shift the emission wavelength into a longer wavelength region for improved compatibility with the employed photodetector.

The specific structures provided herein, the teachings in the Example section and the design criteria and theory provided herein are provided for those skilled in the art to select the appropriate central atoms and luminescent groups for achieving the properties described herein.

Wavelength shifters may be added to the glass compound. These may be employed to provide a higher quantum yield. One example of a wavelength shifter successfully employed in the materials disclosed herein is 9,10-diphenylanthracene (DPA). Other wavelength shifters known to those of skill in the art may also be added to the glass composition, such as 1,4-Bis(5-phenyl-2-oxazolyl)benzene (POPOP).

In an embodiment, homogenous incorporation of the wavelength shifter into the scintillator is done prior to the melt process. In an embodiment, the wavelength shifter or shifters are added to the composition prior to the melt process. They are dissolved in solution and then concentrated in vacuo to produce a solid. The solid can then be used in a melt process.

This strategy unexpectedly provides glass scintillators that exhibit light yields greater than all known plastic and liquid scintillators, and brighter than trans-stilbene single crystals. The use of wavelength shifters in liquid or plastic scintillators may produce large Stokes' shifts and thus long optical attenuation lengths. The use of wavelength shifters for organic molecular crystalline scintillators has not been demonstrated. Such wavelength shifters limit the light yield for crystals with large spectral self-overlap especially for crystals larger in sizes. In contrast, in the glass materials disclosed herein, incorporation of wavelength shifters produces a decrease in the extent of fluorescence self-absorption following the incorporation of the wavelength shifter. This is beneficial for consistent scintillator performance in larger detector volumes.

Another breakthrough in the glass materials disclosed herein is the observation of high scintillation light yields, which has been shown to exceed 1.5 times that of crystalline trans-stilbene. In an embodiment, radioluminescent light yields may be rather high, such as, for example, 10,000 to 25,000 photons/MeVee, exceeding 16,000 photons/MeVee, such as 17,000 to 24,000, or 18,000 to 22,000 as evaluated against EJ-200 plastic scintillators and solution-grown trans-stilbene crystals. Trans-stilbene is one of the brightest known organic scintillators but is difficult to grow in large sizes and is consequently high-cost. The materials disclosed herein provides greater scintillation light yields than trans-stilbene while enabling the potential for rapid, low-cost, and large-scale production via a simple melt casting process.

In addition, to high scintillation light yields the materials described herein are amorphous, robust glass materials that can be sublimated, melt-cast, or formed into large scintillating materials. For example, glass scintillators of sizes on the order of several cubic inches, such as 0.5 to 50 cubic inches, 1 to 20 cubic inches, or 3 to 10 cubic inches can be easily manufactured according to the procedures disclosed herein. In an embodiment, the glass scintillators have thicknesses of 1 micrometer to 1 meter, such as, for example, 10 micrometers to 100 centimeters, or 1 centimeter to 10 centimeters.

In addition, the prepared organic glasses exhibit neutron/gamma pulse-shape discrimination (PSD) and are compatible with wavelength shifters to reduce optical self-absorption effects that are intrinsic to pure materials such as crystalline organics.

In an embodiment, the glass material has a Tg of 25° C. to 300° C., 35° C. to 150° C., or 50° C. to 125° C. The material is not a liquid at room temperature (23° C.). In an embodiment, the material does not behave anisotropically with light. In an embodiment, the material is non-scattering or non-absorbing of light. Furthermore, in an embodiment of the glass materials, under powder X-ray diffraction (PXRD) no discrete X-ray reflections are observed.

In an embodiment, the compounds may have a number average molecular weight of 100 to 2,500 g/mol, such as 500 to 2,200 g/mol, or 800 g/mol to 1,800 g/mol. The compound is not polymeric or oligomeric, that is, it is not a reaction product of multiple repeat units. By these metrics, among others, the glass compound differs from plastic-type scintillators.

The developed materials may be applied to applications that require high luminosity, high electron/hole mobilities, and stable film-forming properties. Two such examples include the fields of organic light emitting diodes (OLEDS) and organic photovoltaics (OPV).

The materials may be prepared by standard organic synthesis techniques. For example, the luminescent organic groups may be functionalized, e.g., lithiated with an alkyl lithium reagent and reacted in solution with the central atom or moiety. The resulting crystals can be purified by flash column chromatography, recrystallization, and/or sublimation.

The purified powder product is then melted, optionally with additives (such as wavelength shifters) dispersed therein, and then cast in a mold and cooled, or drop cast and cooled. The additives may be dispersed by adding them in solution to the material, which may be in a powder or crystalline form, prior to melting.

In another embodiment, the glass material can be formed by sublimation and condensation. In this method, the compound is synthesized and the material is heat-cycled above the sublimation point and condensed in a cooler vessel.

The sublimation method provides the hardest material, and is likely the purest. There is less stress built into the glass structure with this method. However, it should be performed in a vacuum chamber and it is more difficult to achieve glass structures of larger sizes and manufacture them in this method on a large scale compared to the melt forming or drop-casting method.

EXAMPLES

The procedure for synthesizing Examples 1A-3A was as follows. 2-bromo-9,9-dimethylfluorene was prepared according to a known procedure (*J. Phys. Chem. Lett.* 2010, 1, 616-620). A dry 500 mL round bottom flask was charged with a stir bar, 2-bromo-9,9-dimethylfluorene (21.85 g, 79.99 mmol, 3.0 equiv) and THF (180 mL) under argon. The mixture was cooled to −78° C., followed by addition of t-BuLi as 1.7 M solution in n-pentane (100 mL, 6.4 equiv) via cannula transfer over 10 minutes. A dark brown slurry formed. The mixture was stirred for 15 minutes, followed by the addition of MeSiCl$_3$ (3.13 mL, 26.66 mmol) dropwise via syringe. The mixture was slowly warmed to 25° C. and stirred for 12 hours. H$_2$O (100 mL) was added, and the biphasic mixture was extracted with dichloromethane (DCM) (3×50 mL). The combined organics were washed with brine (30 mL), dried with MgSO$_4$, and concentrated in vacuo. The crude was purified via flash column chromatography (0 to 10% DCM in hexanes) followed by recrystallization from toluene to provide 13.2 g of Example 1 as a colorless crystalline solid (79% yield). Examples 2A and 3A were also made according to this method. Further purity was obtained via vacuum sublimation for Example 1C.

Scheme 1 shows the general procedure for the synthesis of Examples 1A to 3A. This formed (tris(9,9-dimethyl-9H-fluoren-2-yl)(methyl)silane) (Example 1A), (tris(9,9-diethyl-9H-fluoren-2-yl)(methyl)silane) (Example 2A), and (tris(9,9-dipropyl-9H-fluoren-2-yl)(methyl)silane) (Example 3a)

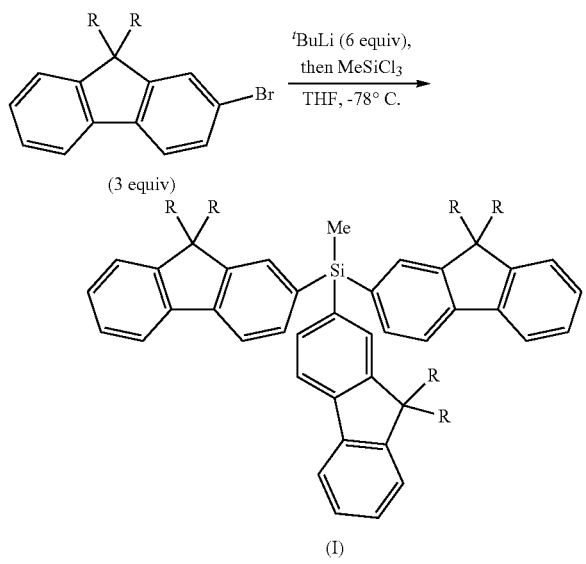

1 R = Me
2 R = Et
3 R = $^n$Pr

Other information on these materials may be found in Carlson, J. and Feng, P., "Melt-Cast Organic Glasses as High-Efficiency Fast Neutron Scintillators" *Nuclear Instruments and Methods in Physics Research A* 2016, 832, 152-157, which is incorporated herein by reference.

Glass Examples

A procedure for casting of a glass was as follows. Example 1A (168 mg) was dissolved in a minimal amount of DCM. In Examples 1D to 3D, DPA (0.04 mg) was added as a solution in DCM. The mixture was concentrated in vacuo to provide a colorless solid. The solid was placed in a vial and the vial was heated with hot air until the solid completely melted. The liquid was poured onto a clean glass slide and allowed to cool. The colorless transparent solid can be used as is for scintillation measurements.

Glass Examples 1B to 3B were prepared as in the procedure above with the following parameters and equipment. The different samples were prepared to confirm that the light collection efficiency and corresponding light yields remained constant for these small sample sizes in the experimental configuration described herein. FIG. 1 shows a photograph of two forms of Example 1B; the 1 cm top circular material was drop-cast from the liquid onto a glass slide, whereas the 2 cm cube shown in the inset was melted and cooled in a silicone mold. The data for Examples 1B to 3B shown in Table I were formed via the method described above.

A reference sample of EJ-200 (a commercial plastic scintillator) was obtained from Eljen Technologies. The trans-stilbene reference sample was prepared according to a technique described by Carman, et al., "The Effect of Material Purity on the Optical and Scintillation Properties of Solution-Grown Trans-Stilbene Crystals" *J. Cryst. Growth* 2013, 368, 56-61, which is incorporated herein by reference. This method comprises synthetic preparation from styrene, followed by crystal growth from anhydrous anisole.

Table I shows a summary of photoluminescence quantum yields and gamma-ray scintillation light-yield data (relative to trans-stilbene) for Examples 1A to 3A (crystalline state) and 1B to 3B (glassy state).

Steady-state spectra, quantum-yields, and time-resolved photoluminescence measurements were collected using a Horiba Jobin-Yvon Fluorolog FL3-21 fluorescence spectrometer equipped with an integrating sphere attachment. Data were collected on powder samples at 90° angle of incidence for steady-state spectra and time-resolved measurements, and in the front-facing geometry for quantum-yield data. Differential scanning calorimetry data were collected using a Mettler Toledo DSC 822 instrument and processed using the STARe SW 12.10 software package. A heating and cooling scan rate of +/−10° C. was used during data acquisition. Powder X-ray diffraction data were obtained using a PANanalytical Empyrean instrument equipped with a 40 kV Cu K-alpha source and an XY-rotating sample stage. 662 keV gamma-ray scintillation pulse-height spectra were obtained for bulk samples using a $^{137}$Cs source. All samples were evaluated using an Electron Tubes 9124-QB bialkali photomultiplier tube biased at 1000 V. Pulses were digitized using a 600 MHz, 12-bit LeCroy HRO 66Zi oscilloscope and histogrammed using a 500 ns integration time for scintillation pulse-height measurements. Neutron/gamma pulse-shape discrimination data were obtained using a similar experimental configuration but processed off-line using the charge-comparison method. The charge-comparison PSD parameters were optimized for each sample, comprising the prompt/delayed cutoff time and total integration time.

TABLE I

| Compound | PL Quantum Yield (Φ) | 662 keV Relative L.Y. | 33 keV Relative L.Y. |
| --- | --- | --- | --- |
| Trans-stilbene-Crystal (Control for light yield) | 0.62 | 1.00 | 1.00 |
| EJ-200-Plastic (Comparison) | 0.55 (PVT = 0.17) | 0.78 | 0.89 |
| Example 1A (Crystal) | 0.46 | * | 1.26 |
| Example 2A (Crystal) | 0.53 | * | 1.21 |
| Example 3A (Crystal) | 0.78 | * | 1.44 |
| Example 1B (Glass) | 0.39 | 1.02 | 0.97 |
| Example 2B (Glass) | 0.57 | 0.74 | 0.83 |
| Example 3B (Glass) | 0.48 | 0.59 | 0.68 |

*Not observed due to small crystal size.

Example 1C, a sublimed Example, was also formed from purified crystals. Crystals obtained from recrystallization were purified via sublimation, i.e., sublimed then condensed under vacuum using an apparatus obtained from Chemglass using techniques known to those skilled in the art to obtain samples up to 3 mm in diameter.

Fluorescence timing, as well as other photoluminescence measurements were performed on Additional photoluminescence measurements were performed on the glasses of Examples 1B to 3B and 1C.

Figure 2:
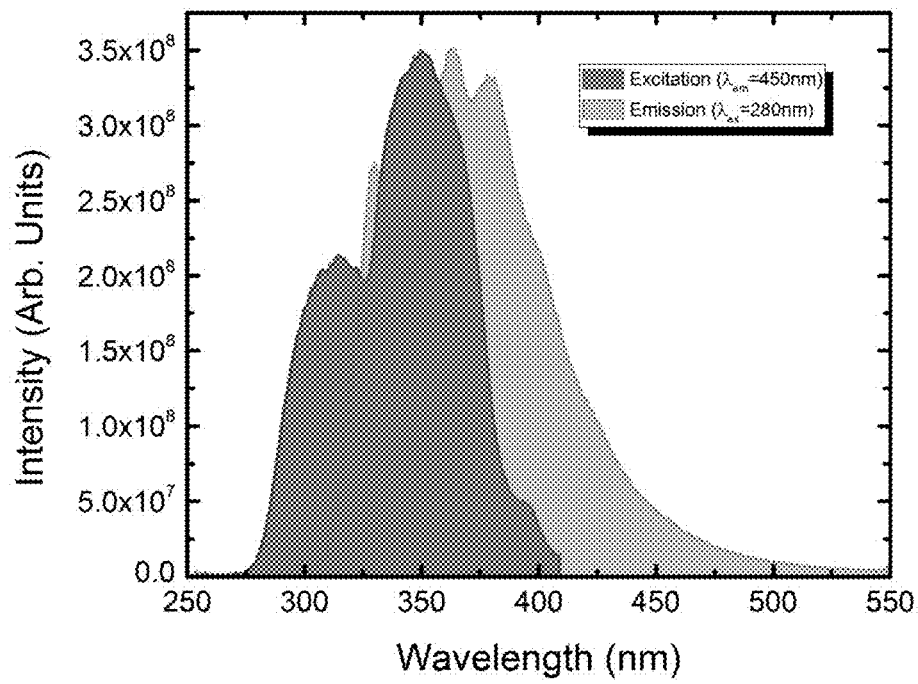
FIG. 2 is a pair of plots showing the excitation and emission photoluminescence spectra for sublimed glass (top) and melt-cast glass (bottom) formed from Example 1A.
Figure 2:
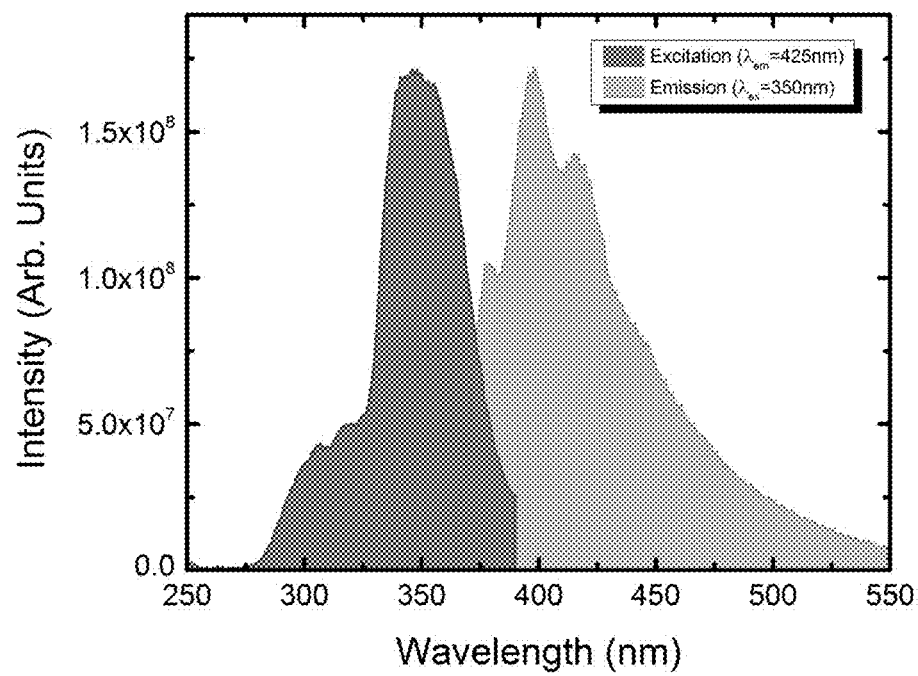

Steady-state excitation and emission spectra for glass Example 1B are provided in FIG. 2, illustrating properties that are dependent upon the preparation method. Data in the top plot was obtained on a glass prepared via sublimation (Example 1C), whereas the data in the bottom figure was obtained for a melt-cast glass (Example 1B). The emission spectra reveal a 38 nm blue-shift in the peak emission wavelength for sublimed (Example 1C) versus melt-cast glasses (Example 1B).

The presence of fine structure in both spectra suggests that the shift is not due to excimer or exciplex formation but instead is associated with the activation of different phonon modes on the discrete fluorene chromophores. The spectral shift is imposed by differences in molecular packing and this assignment is further supported by the presence of common vibronic transitions and comparable fluorescence lifetimes ($\tau_1$=0.8 ns [56%], $\tau_2$=2 ns [44%]) observed for both forms. Respective fluorescence quantum yields of 0.39 and 0.47 were obtained for equivalently pure samples of sublimed glass (Example 1C) and melt-formed glass (Example 1B). This is somewhat surprising considering the immense spectral overlap for the sublimed glass (Example 1C). Further preparations described below are of Examples 1B to 3B (glassy state) due to the improved scalability of this method used to make those examples.

Examples 1D to 3D: Wavelength Shifters

A fundamental limitation that contributes to the limited light yields of plastic and liquid scintillators is a low fluorescence quantum yield for the host matrix, which ranges from 0.12 for polystyrene/polyvinyltoluene to 0.17 for toluene. Equations 1 and 2 indicate the significance of this limitation, as the efficiency (E) of fluorescence resonant energy transfer (FRET) is associated with the fluorescence quantum yield of the donor ($Q_D$). Other variables in these equations include the donor-acceptor distance (r), dipole orientation factor ($\kappa^2$), Avogadro's number ($N_A$), refractive index of the medium (n), and spectral overlap integral (J).

$$E = \frac{1}{1 + (r/R_0)^6} \quad (1)$$

$$R_0^6 = \frac{9(\ln 10)}{128\pi^5 N_A} \frac{\kappa^2 Q_D}{n^4} J \quad (2)$$

High fluorescence quantum yields and efficient FRET energy transfer are therefore pre-requisites for high-efficiency organic scintillator mixtures since the final step of energy conversion always proceeds through the fluorescent excited state. It is worth noting that a similar FRET constraint is not required for single-component scintillators such as organic crystals since there is no donor or acceptor. However, crystalline scintillators intrinsically suffer from a different type of performance degradation due to self-absorption of the overlapping excitation and emission spectra. This limitation is also particularly evident in the sublimed glass of Example 1C.

For the above reasons, compositions formed from Examples 1A to 3A into glass Examples 1B to 3B were evaluated as a new type of solid-state and transparent host matrix for wavelength shifting dyes. The fluorescence quantum yields for glass Examples 1B to 3B are between 0.39 and 0.57 (See Table I), which is between 2-5 times that of typical liquid and plastic scintillator matrices. These higher quantum yields provide the possibility for enhanced FRET and scintillation light yields. The wavelength shifter 9,10-diphenylanthracene (DPA) was selected for this study due to good spectral overlap and strong molar absorptivity in the donor emission range. DPA was added in solution to the material prior to melting.

As shown in Table II, DPA concentrations in the range of 0.02 to 0.05% by weight of the total composition were evaluated for solubility and fluorescence/scintillation enhancement.

TABLE II

|  | Compound | PL Quantum Yield ($\Phi$) | 662 keV Relative L.Y. | 33 keV Relative L.Y. |
| --- | --- | --- | --- | --- |
| Example 1D-Glass | (Example 1A + 0.02% DPA) | 0.89 | 1.03 | 0.93 |
| Example 2D-Glass | (Example 2A + 0.02% DPA) | 0.66 | 1.11 | 1.11 |
| Example 3D-Glass | (Example 3A + 0.05% DPA) | 0.67 | 1.23 | 1.18 |

The results for wavelength-shifted organic glass materials are summarized in Table II, revealing fluorescence quantum yields as high as 0.89 and 662 keV gamma-ray light yields of up to 123% trans-stilbene. The absence of any aggregation-induced spectral shifts for 0.02 to 0.05% DPA in glasses of Examples 1D to 3D indicates that the wavelength shifter is soluble at these concentrations. This observation is consistent with the lack of any detectable phase separation or particle-induced light scattering in the samples.

Figure 3:
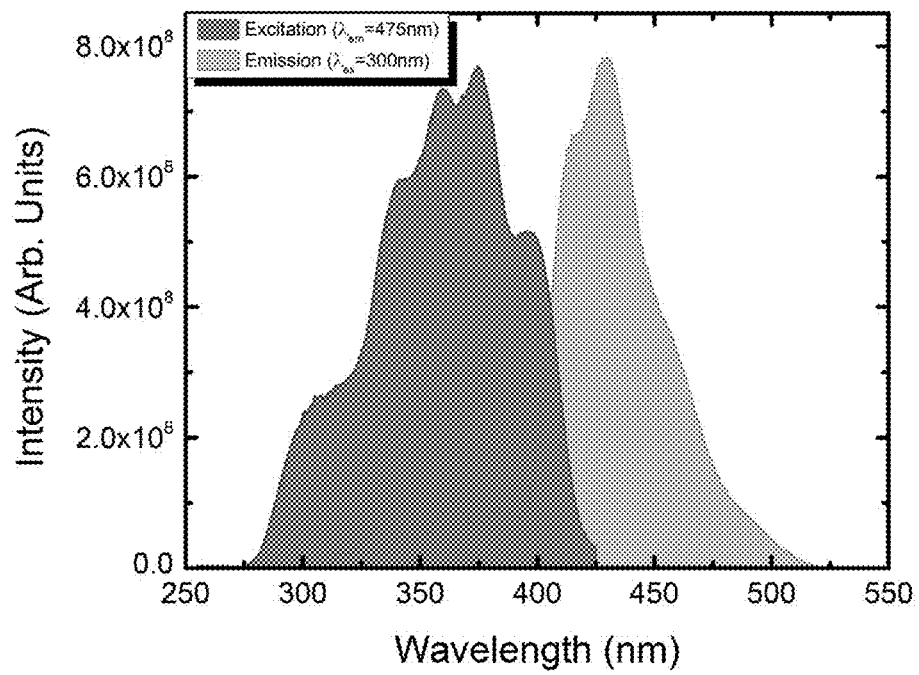
FIG. 3 is a pair of excitation and emission PL spectra for Example 1D in the glassy state containing 0.02% (w/w) 9,10-diphenylanthracene (DPA) (top), and Example 3D (0.05% DPA) (bottom), illustrating differing amounts of spectral self-overlap.
Figure 3:
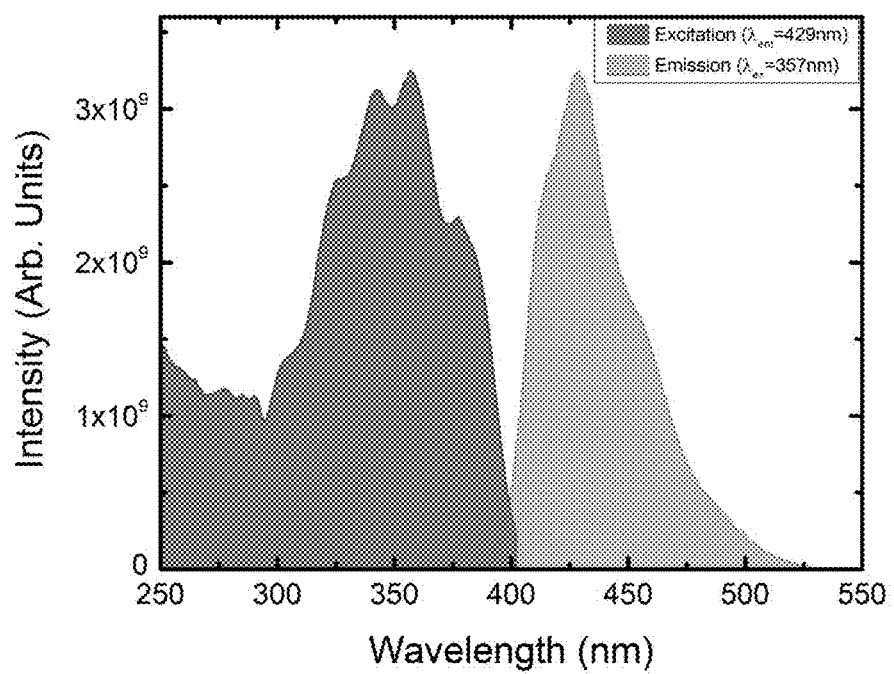

FIG. 3 provides the photoluminescence spectra for DPA-containing Examples 1D and 3D. The spectra reveal a decrease in the extent of fluorescence self-absorption following the incorporation of the wavelength shifter. Very little self-overlap is evident in the excitation and emission spectra for 0.05% DPA in Examples 3D (FIG. 3, bottom), as required for consistent scintillator performance in larger detector volumes.

Differential Scanning Calorimetry

Figure 7:
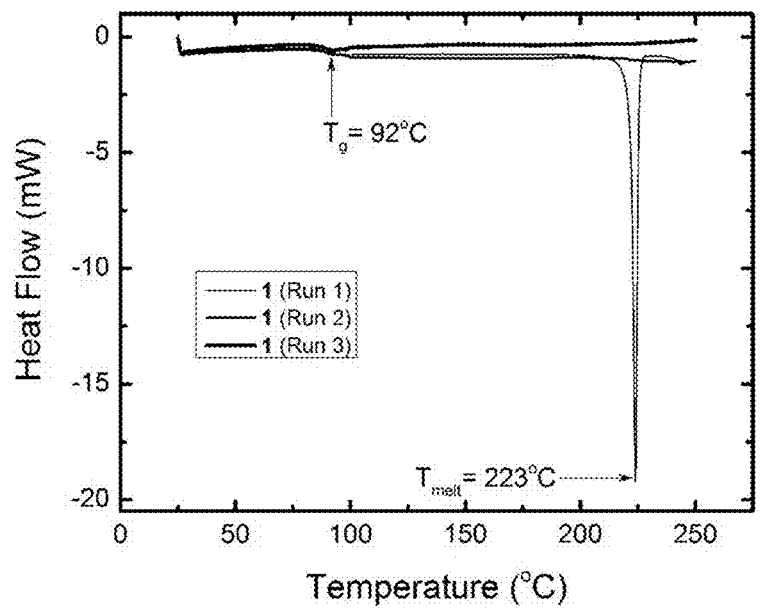
FIGS. 7-10 show DSC traces for Examples 1A, 2A, 6, and 7, respectively.
Figure 8:
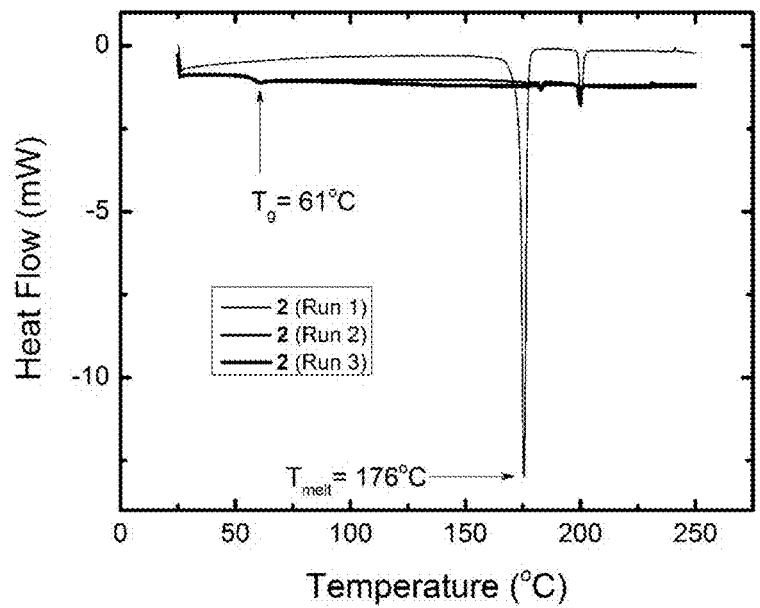
Figure 9:
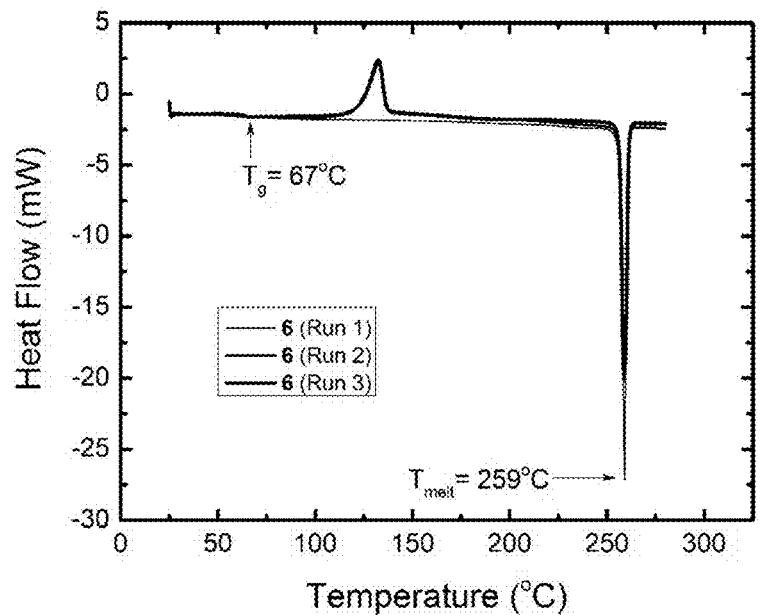
Figure 10:
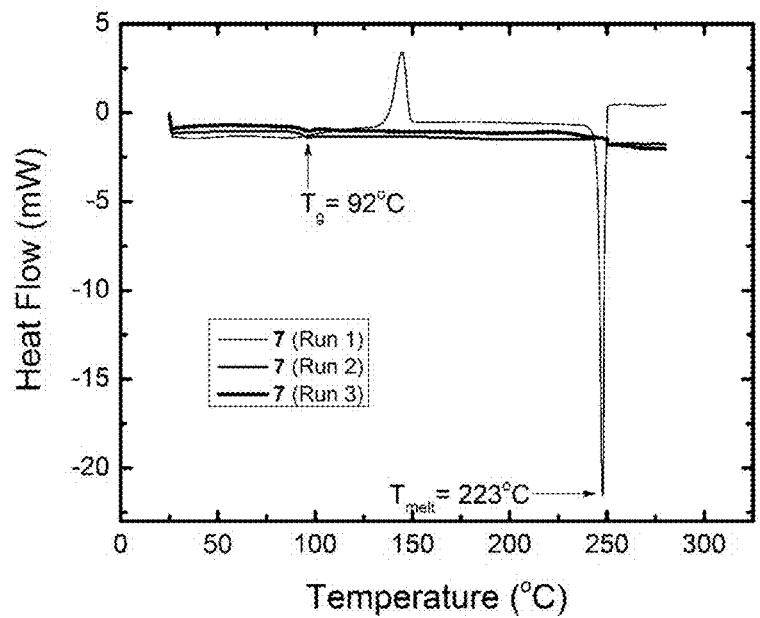

Differential scanning calorimetry (DSC) data were collected for Examples 1A to understand the crystallization, melting, and glass-formation properties of these materials. A representative dataset is provided in FIG. 7 for Example 1A. (The data obtained in the crystalline form was representative of the glass examples as well. In fact, in the DSC, as the samples heat up, crystals turn into liquid (run 1); when it cools it becomes the glass. So run 2 and 3 were technically conducted on Examples 1B-3B.)

The scans indicate that the crystalline as-synthesized powder undergoes a melting transition in the first run, as evident by the well-defined endotherm at 223° C. Subsequent runs were performed using the same experimental protocol after cooling the sample back to room temperature. Conversion to an amorphous material is indicated by the absence of a melting transition in the runs 2 and 3 and the concomitant appearance of a glass-transition at 92° C. This $T_g$ value is comparable to that of polystyrene and higher than polyvinyltoluene, both of which are used in commercial plastic scintillators.

Qualitatively similar behavior was observed for Examples 2A and 3A, as summarized in Table III. The $T_g$ value of Example 3A was not observed under the performed experimental conditions due to sample recrystallization at the performed cooling rate. To observe the $T_g$, flash cooling of the melt provided a glassy sample which could then be analyzed using DSC.

TABLE III

| Compound Number | $T_g$ (° C.) | $T_{melt}$ (° C.) |
| --- | --- | --- |
| 1A | 92 | 223 |
| 2A | 63 | 175 |
| 3B | 55* | 192 |

*Observed after quench cooling of the melt

Scintillation Pulse-Height Spectra

Figure 4:
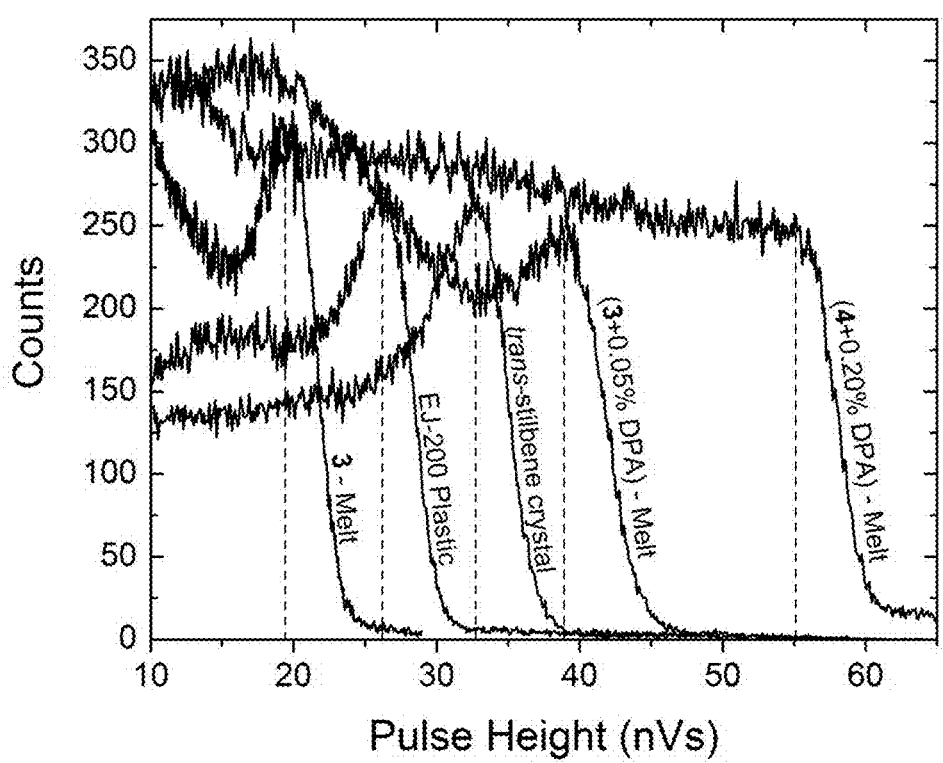
FIG. 4 shows a $^{137}$Cs scintillation pulse-height spectra obtained for trans-stilbene and EJ-200 reference samples and two melt-cast glasses Example 3B and 3D.

Scintillation pulse-height spectra (PHS) were collected using $^{137}$Cs gamma-rays for glass samples of Examples 1B-3B, summarized in Table I. These measurements were performed to evaluate the light yields relative to EJ-200 plastic and trans-stilbene crystal reference materials. A comparison of the 662 keV gamma-ray pulse-height spectra is provided in FIG. 4 for Examples 3D and 4 (defined below) in glass form containing DPA. The light yields for small (approximately 1-2 mm$^3$) crystals of Examples 1B-3B were first evaluated using the 33 keV X-rays emitted from $^{137}$Cs. The observed photoelectric absorption peak for each sample was found to be greater than for the two reference materials, which provided a promising indication of the potential for these compounds. Corresponding spectra obtained for bulk melt-cast glasses of these materials revealed somewhat lower light yields, although the larger size of these samples (about 0.5 cm$^3$) also permitted measurement of 662 keV gamma-rays.

The 662 keV spectra for pure melts of Examples 1A and 2A do not provide a clearly resolved Compton maximum (not shown), which suggests incomplete light collection and/or poor energy resolution. This finding is corroborated by the strong self-absorption of undoped glasses of these two materials (FIG. 2).

Subsequent light-yield measurements performed on glasses containing DPA wavelength shifter at 0.02-0.05% w/w reveal improvements in the light-yield and energy resolution.

Figure 5:
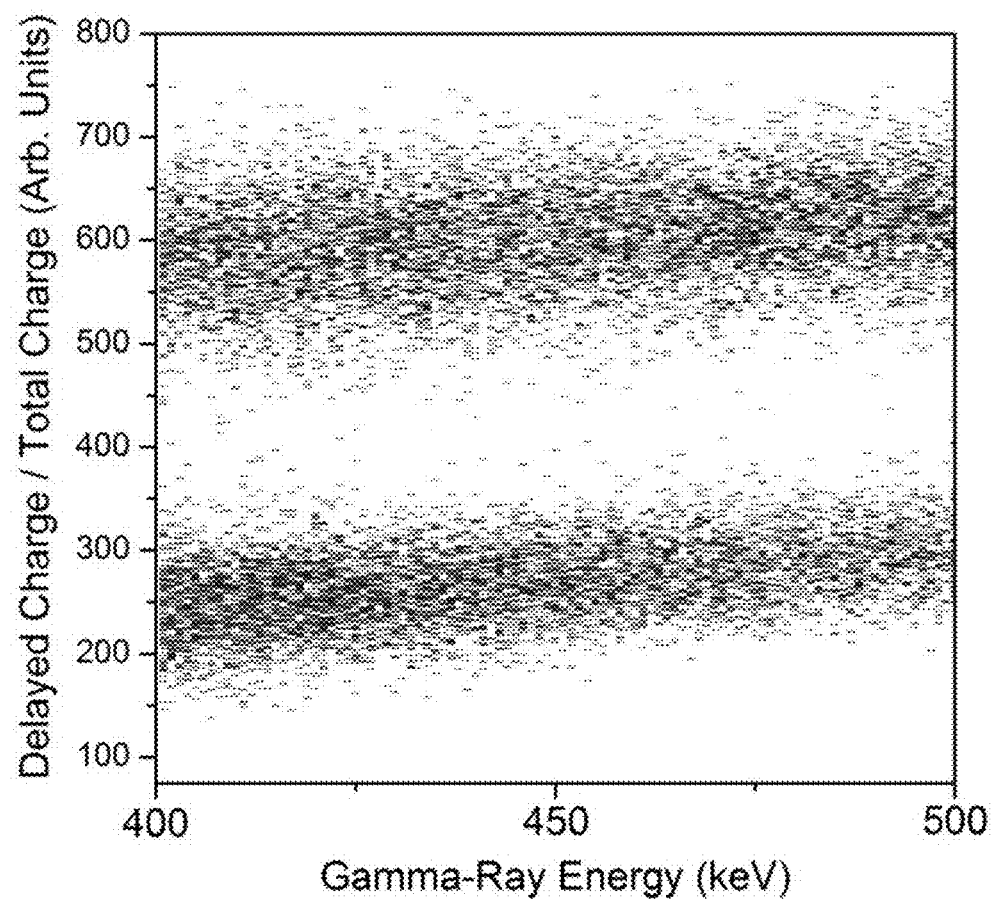
FIG. 5 is a neutron/gamma pulse-shape discrimination scatter plot for a melt-cast glass of Example 3D in the energy range of 400-500 keVee.

FIG. 5 shows a $^{137}$Cs scintillation pulse-height spectra obtained for trans-stilbene and EJ-200 reference samples and two melt-cast glasses Example 3B and 3D (with DPA). The dotted lines serve as guides to the eye for the respective Compton maxima.

It is evident from FIG. 5 that the DPA-containing glass of Example 3D exhibits a different pulse shape than the two reference materials. The higher occurrence of events in the lower energy region of the spectrum has been attributed to luminescence from high energy electrons originating from the cesium source. In subsequent experiments (not shown) with increased shielding this effect completely diminished.

Pulse-Shape Discrimination

Pulse-shape discrimination (PSD) measurements were conducted on the prepared organic glasses using an unshielded AmBe neutron/gamma source. Prior work has shown that PSD may be easily disrupted by the presence of small amounts of impurities, disorder, or defects in the material. For example, Carman, et al., "The Effect of Material Purity on the Optical and Scintillation Properties of Solution-Grown Trans-Stilbene Crystals, *J. Cryst. Growth* 2013, 368, 56-61, has shown that the presence of 0.5% 2-phenylindene impurity in trans-stilbene led to a 42% reduction in the neutron/gamma separation efficiency. Similarly, the disordered/amorphous structure of plastic scintillators typically precludes PSD unless very high dye concentrations or triplet-harvesting compounds are added. Perhaps for this reason, organic glasses have never been assessed for their scintillation properties. However, the surprising results shown in FIGS. 5 and 6 show that these materials are indeed capable of efficient neutron/gamma particle discrimination.

FIG. 5 is a neutron/gamma pulse-shape discrimination scatter plot for a melt-cast glass of Example 3D in the energy range of 400-500 keVee. The upper distribution corresponds to fast neutron events and the lower distribution gamma-ray events.

Figure 6:
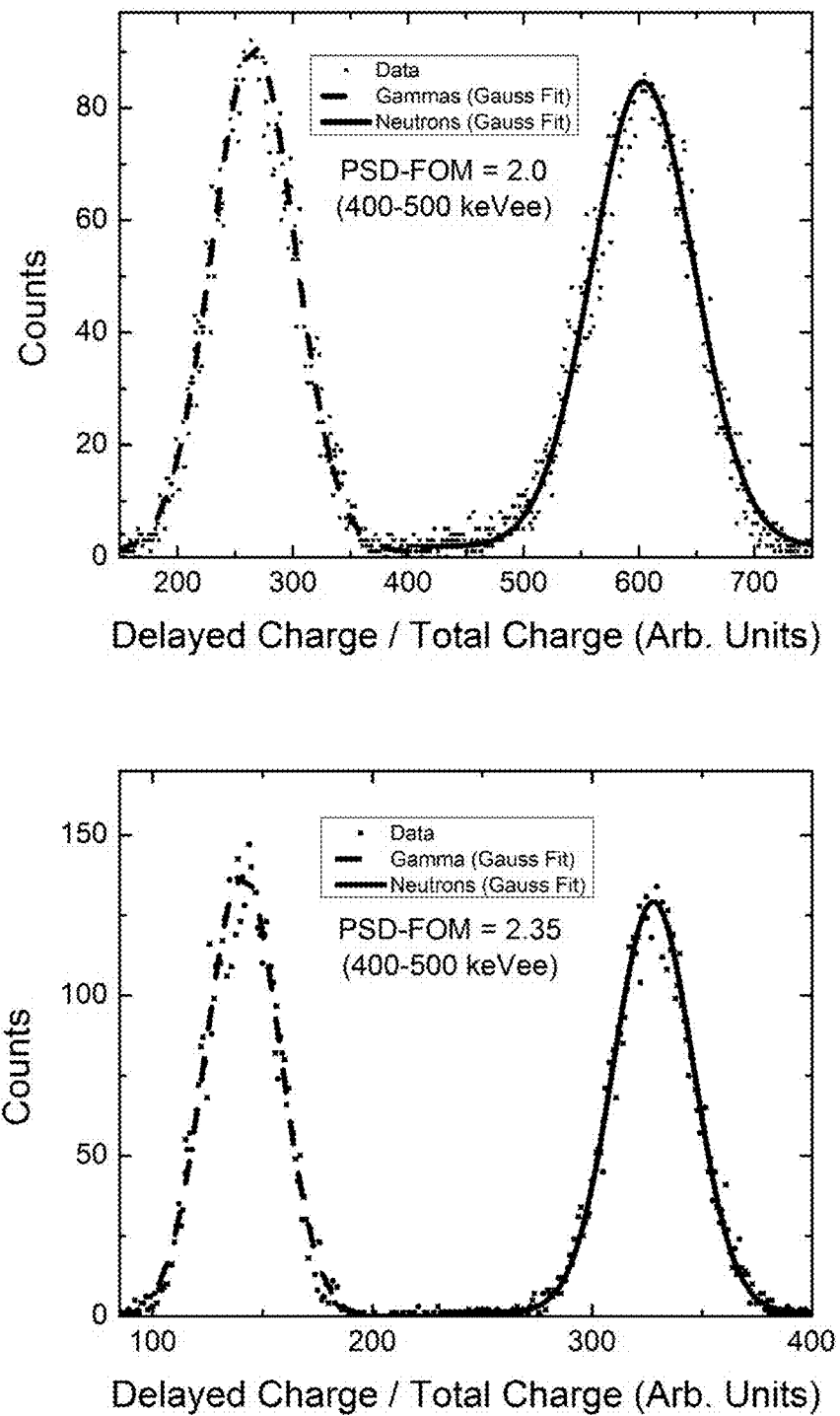
FIG. 6 shows neutron/gamma pulse-shape discrimination histograms obtained for a melt-cast glass of Example 3D (top) and a trans-stilbene single crystal (bottom) in the energy range of 400-500 keVee.

FIG. 6 shows neutron/gamma pulse-shape discrimination histograms obtained for a melt-cast glass of Example 3D (0.05% DPA) (top) and a trans-stilbene single crystal (bottom) in the energy range of 400-500 keVee. The solid line and dashed line correspond to Gaussian fits to the data for fast neutrons and gamma-rays, respectively.

The pulse-shape discrimination figure-of-merit (PSD-FOM) was calculated to quantify the neutron/gamma separation efficiency at a given energy threshold. The PSD-FOM is defined by the separation between neutron and gamma events divided by the sum of the FWHM values for the respective histogram distributions shown in FIG. 6. A PSD-FOM value of 2.0 was obtained in the energy range of 400 to 500 keVee for a melt-cast glass of Example 3D (0.05% DPA), which compares to a corresponding PSD-FOM value of 2.35 for a solution-grown trans-stilbene reference crystal. In both cases, the charge comparison method was employed using integration time intervals that were optimized for each material. The best PSD-FOM was obtained for Example 3D using a prompt/delayed cutoff of 40 ns after the pulse leading edge and a total integration time of 300 ns. Optimization of these parameters for the trans-stilbene reference sample led to a prompt/delayed cutoff of 30 ns and a total integration time of 400 ns.

It was observed that Examples 1-3 yielded PSD in both crystalline (1A-3A) and glass phases (1B-3B and 1D to 3D).

Examples 4-7

Examples 4-5 were synthesized following the procedure disclosed for Examples 1B-3B modified with different starting materials. Examples 6 and 7 were prepared in a similar fashion, using either t-butyltrichlorosilane or trichlorophosphine instead of methyltrichlorosilane. The compounds in Examples 4-7 are identified below.

Example 4 (tris(9,9-diisobutyl-9H-fluoren-2-yl)(methyl)silane)

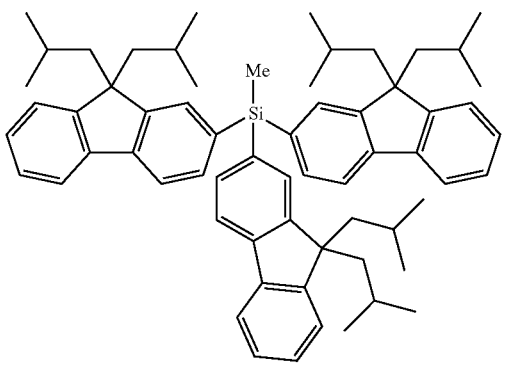 [SMILES: CC(C)CC1(CC(C)C)c2ccccc2-c2ccc([Si](C)(c3ccc4c(c3)C(CC(C)C)(CC(C)C)c3ccccc3-4)c3ccc4c(c3)C(CC(C)C)(CC(C)C)c3ccccc3-4)cc21]

Example 5 (tert-butyltris(9,9-dimethyl-9H-fluoren-2-yl)silane)

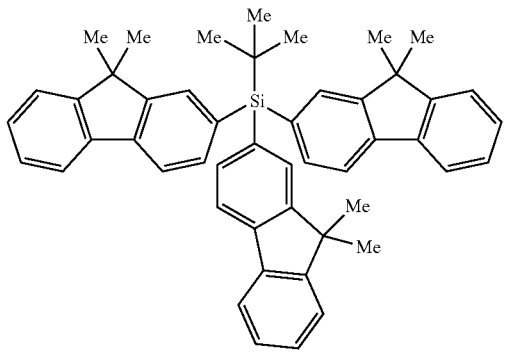

Example 6 (tert-butyltris(9,9-diethyl-9H-fluoren-2-yl)silane)

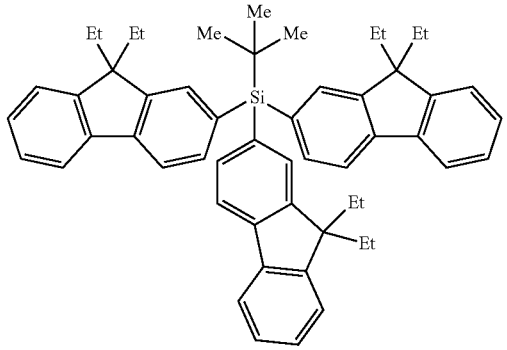 [SMILES: CCC1(CC)c2ccccc2-c2ccc([Si](c3ccc4c(c3)C(CC)(CC)c3ccccc3-4)(c3ccc4c(c3)C(CC)(CC)c3ccccc3-4)C(C)(C)C)cc21]

Example 7 (tris(9,9-diethyl-9H-fluoren-2-yl)phosphine oxide)

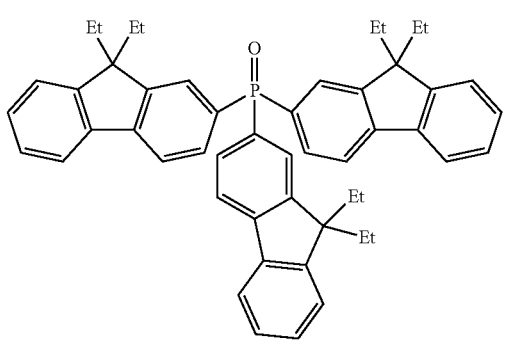

FIGS. 8-11 show DSC traces for Examples 1A, 2A, 6, and 7, respectively. The increasing line width corresponds to the initial, second, and third heating runs, respectively. Negative peaks represent endothermic transitions (i.e. melting, Tg), whereas positive peaks represent exothermic transitions (i.e. recrystallization). The range of behaviors illustrate the effects that substitution of various atomic positions has upon the observed thermal properties.

The glassy nature of Examples 1-7 was quantified by differential scanning calorimetry (DSC), powder X-ray diffraction (pXRD) data, and optical transmission measurements. The absence and/or loss of a melting endotherm in the DSC and the concomitant appearance of a glass transition ($T_g$) endotherm provide evidence for the conversion from a crystalline material to an amorphous glass. This was confirmed using pXRD, for which no discrete X-ray reflections were observed for the amorphous organic glasses.

Furthermore, the amorphous nature of the obtained organic glasses was characterized optically, for which the melted glasses showed high optical transparency after cooling. This is associated with the random orientation of molecules in the glass and is a preferred attribute for a scintillator due to the ability to collect and detect (using a photodetector) optical photons generated within the macroscopic volume of the scintillating material. This is in contrast to crystalline materials, which strongly scatter light at grain boundaries upon recrystallization from the melt and cannot be used as bulk detectors except in single crystalline form.

Additional Example Compound Structures

Representative trigonal pyramidal or tetrahedral structures for the glass scintillators are shown below. Many of these examples exhibit high resistance towards crystallization. All of the structures below were made and evaluated for their scintillation performance and formed a glass material.

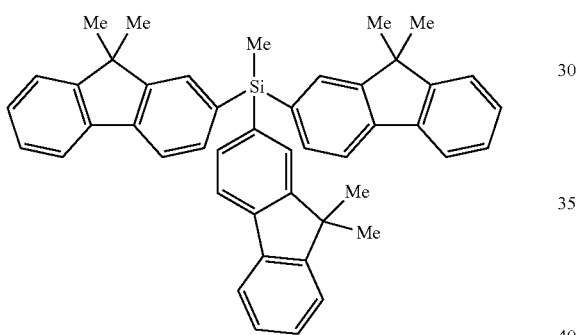

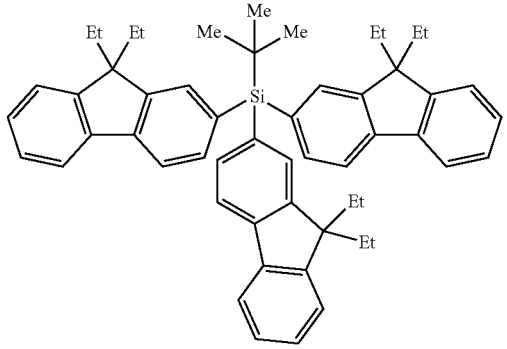

-continued

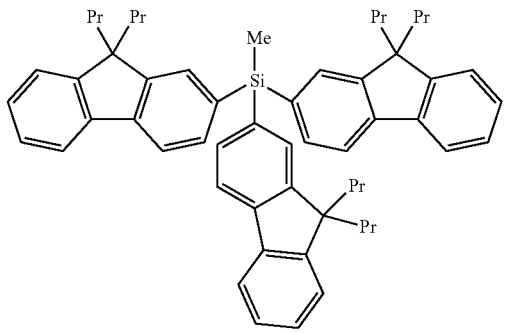 [SMILES: CCC1(CC)c2ccccc2-c2ccc(P(=O)(c3ccc4c(c3)C(CC)(CC)c3ccccc3-4)c3ccc4c(c3)C(CC)(CC)c3ccccc3-4)cc21]

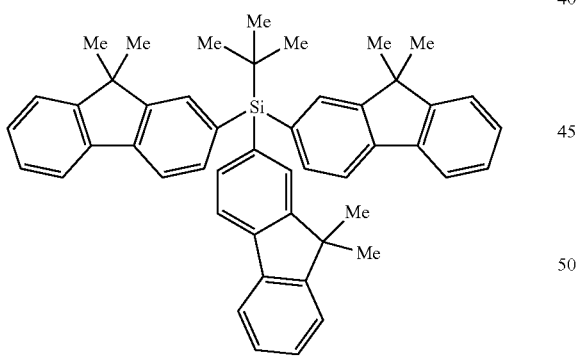

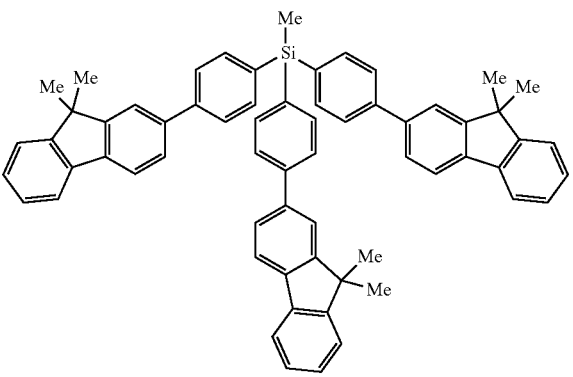

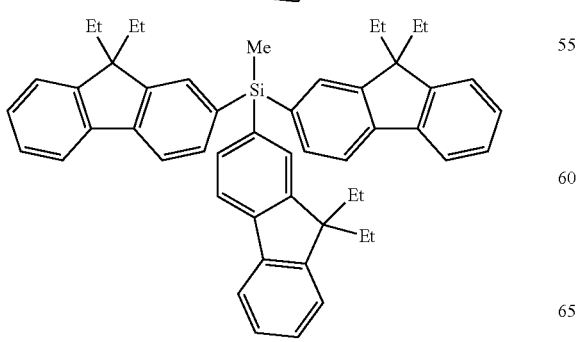

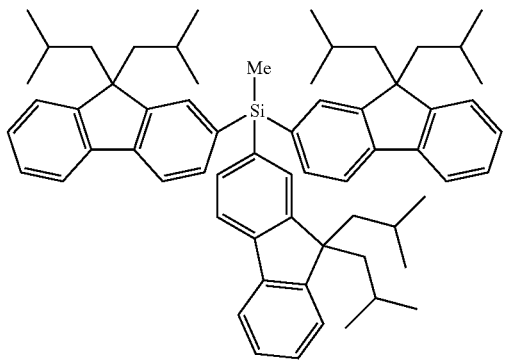

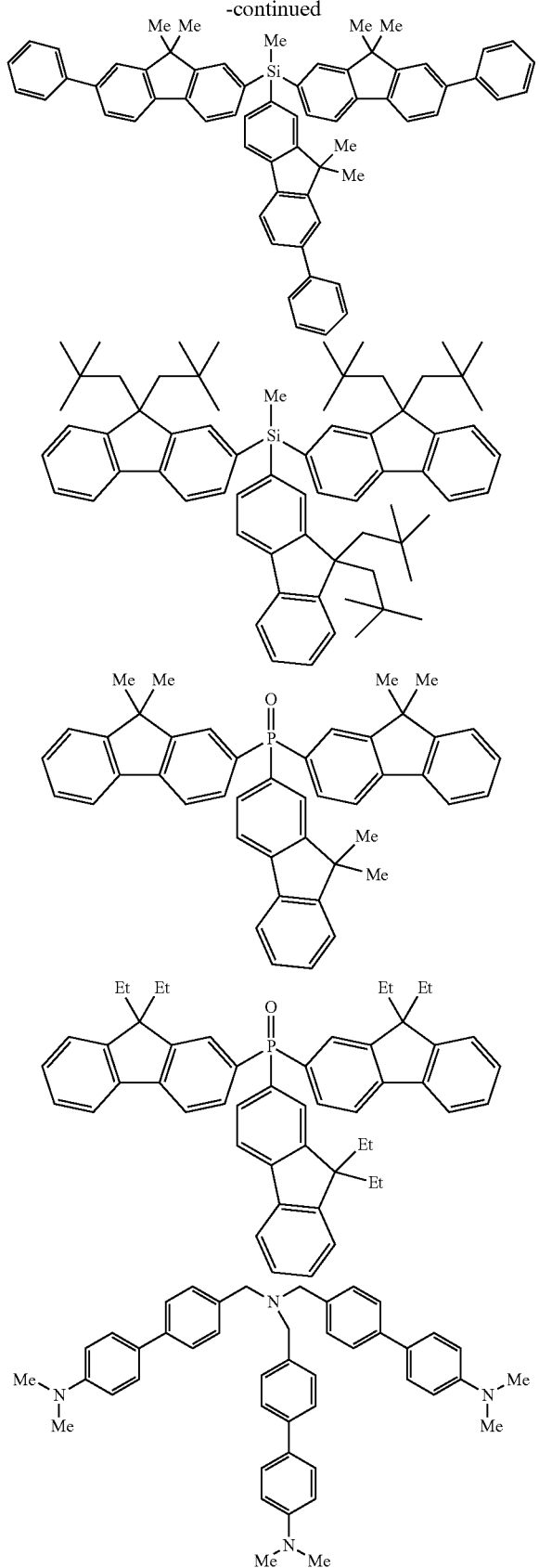

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the details description or the claims, such term is intended to be inclusive in a manner similar to the term "comprising" as "comprising" is interpreted when employed as a transitional word in a claim. The term "consisting essentially" as used herein means the specified materials or steps and those that do not materially affect the basic and novel characteristics of the material or method. All percentages and averages are by weight unless the context indicates otherwise. The articles "a," "an," and "the," should be interpreted to mean "one or more" unless the context indicates the contrary.

It is claimed:

1. A glass scintillator material comprising:
a compound, including:
a central species selected from the group consisting of: silicon, phosphorus, nitrogen, tin, germanium; an oxide, salt, or alkyl salt of silicon, phosphorus, nitrogen, tin, or germanium; or a rotationally symmetric organic species, or combination of any of the these;
a luminescent organic group bonded to the central species or to an optional organic linker group;
the optional organic linker group, if present, is bonded to the central species and the luminescent organic group;
wherein the compound is in the form of an amorphous glass and is capable of generating luminescence in the presence of ionizing radiation.

2. The glass scintillator material of claim 1, wherein the luminescent organic group is selected from the group consisting of: quaterphenyl, terphenyl, trans-stilbene, naphthalene, anthracene, truxene, triphenylene, 1,3,5-triphenylbenzene, spirobifluorene, fluorene, carbazole, coumarin, anthracene, naphthalene, biphenyl, coumarin, phenyloxazole, phenyloxadiazole, 2,5-diphenyloxazole, 9,9'-dialkylfluorene, 9,9'-diarylfluorene, 2-aryl-9,9'-dialkylfluorene, 2-aryl-9,9'-diarylfluorene, 7-aryl-9,9'-dialkylfluorene, 7-aryl-9,9'-diarylfluorene, 7-alkyl-9,9'-dialkylfluorene, 7-alkyl-9,9'-diarylfluorene, 9,10-diphenylanthracene, 2,5-diphenyl-1,3,4-oxadiazole, p-terphenyl, salicylic acid, and methyl salicylate and analogs thereof.

3. The glass scintillator material of claim 1, wherein the central species is adamantane, benzene, truxene, triphenylene, spiro-bifluorene, and analogs thereof.

4. The glass scintillator material of claim 1, wherein the central species and the luminescent organic group are selected to inhibit pi-pi stacking in the compound and an overall three-dimensional structure of the compound inhibits pi-pi stacking.

5. The glass scintillator material of claim 1, wherein the central species is selected from phosphine oxide, tin, or silicon, and the luminescent organic group is an aromatic group.

6. The glass scintillator material of claim 1, wherein the luminescent organic group is a polycyclic group comprising one or more benzylic carbons and at least one benzylic carbon is substituted with an organic group.

7. The glass scintillator material of claim 6, wherein the organic group contains a fluorene or biphenyl sub-unit possessing alkylation at a benzylic, or double benzylic position.

8. The glass scintillator material of claim 1, wherein the central atom or species bonds to the luminescent organic groups in a tripodal or tetrahedral geometry.

9. The glass scintillator material of claim 6, wherein the compound has C3 rotational symmetry.

10. The glass scintillator material of claim 1, wherein the compound produces a light yield of 15,000 photons/MeVee to 40,000 photons/MeVee with a trans-stilbene reference.

11. The glass scintillator material of claim 1, wherein the compound has a glass transition temperature of 25° C. to 300° C.

12. The glass scintillator material of claim 1, further comprising a wavelength shifter.

13. The glass scintillator material of claim 1, wherein the amorphous glass has a thickness of 1 micrometer to 1 meter.

14. The glass scintillator material of claim 1, wherein the amorphous glass is capable of neutron and gamma pulse-shape discrimination, at 33 keVee to 30 MeVee.

15. A method of making a compound, comprising:
functionalizing a luminescent organic group;
reacting the functionalized luminescent organic group with a central species to produce a compound with tripodal or tetrahedral geometry wherein one or more of the luminescent organic groups are bonded to the central species;
wherein the central species is selected from the group consisting of: silicon, phosphorus, nitrogen, tin, germanium; an oxide, salt, or alkyl salt of silicon, phosphorus, nitrogen, tin, or germanium; or a rotationally symmetric organic species, or combination of any of these;
wherein the luminescent organic group is selected to inhibit pi-pi stacking of the compound.

16. The method of claim 15, further comprising melting the compound and cooling the compound or sublimating the compound and condensing the compound to form an amorphous glass.

17. The method of claim 15, wherein the luminescent organic group is a polycyclic group comprising one or more benzylic carbons and at least one benzylic carbon is substituted with an organic group that is selected to inhibit pi-pi stacking in the compound.

18. The method of claim 16, further comprising adding a wavelength shifter to the material prior to the cooling step.

19. A method for conducting scintillation, the method comprising:
generating luminescence with a glass scintillating compound in the presence of ionizing radiation, the glass scintillating compound including:
a central species selected from the group consisting of: silicon, phosphorus, nitrogen, tin, germanium; an oxide, salt, or alkyl salt of silicon, phosphorus, nitrogen, tin, or germanium; or a rotationally symmetric organic species, or combination of any of these;
a luminescent organic group bonded to the central species or to an optional organic linker group;
the optional organic linker group if present is bonded to the central species and the luminescent organic group;
wherein the compound is in the form of an amorphous glass and is capable of scintillation;
detecting photons from the glass scintillating compound with a photodetector.

20. The method of claim 19, further comprising conducting neutron and gamma pulse-shape discrimination with the glass scintillating compound at 33 keVee to 30 MeVee.

* * * * *